United States Patent [19]

Dolhyj et al.

[11] 4,299,987

[45] Nov. 10, 1981

[54] PROCESS FOR PRODUCING BENZO-PHENONE FROM 1,1-DIPHENYLETHANE (OR 1,1-DIPHENYLETHYLENE) USING ANTIMONATE CATALYSTS

[75] Inventors: Serge R. Dolhyj, Parma; Louis J. Velenyi, Lyndhurst, both of Ohio

[73] Assignee: The Standard Oil Company, Cleveland, Ohio

[21] Appl. No.: 851,011

[22] Filed: Nov. 14, 1977

[51] Int. Cl.$^3$ .............................................. C07C 45/36
[52] U.S. Cl. ................................. 568/321; 260/465 R; 260/465 D; 260/465 F; 260/465 H; 260/546; 560/52
[58] Field of Search ............... 260/590 R, 591, 597 R, 260/604 R, 465 R, 465 D, 465 F, 465 H, 546; 568/321; 560/52

[56] References Cited

U.S. PATENT DOCUMENTS

| | | | |
|---|---|---|---|
| 3,201,476 | 8/1965 | Baker et al. | 260/597 R |
| 3,424,789 | 1/1969 | Schulz et al. | 260/591 |
| 3,431,292 | 3/1969 | Callahan et al. | 260/604 R |
| 3,435,061 | 3/1969 | Grasselli et al. | 260/599 |
| 3,899,537 | 8/1975 | Holtz | 260/591 |
| 3,935,272 | 1/1976 | Chapurlat | 260/597 R |
| 3,946,077 | 3/1976 | Thiel et al. | 260/597 R |
| 3,946,081 | 3/1976 | Wedemeyer et al. | 260/597 R |

*Primary Examiner*—Natalie Trousof
*Assistant Examiner*—James H. Reamer
*Attorney, Agent, or Firm*—Gary R. Plotecher; Herbert D. Knudsen; Larry W. Evans

[57] ABSTRACT

1,1-diphenylethane or 1,1-diphenylethylene is oxidized to benzophenone by contacting the 1,1-diphenylethane or 1,1-diphenylethylene and oxygen with an antimonate catalyst.

1 Claim, No Drawings

PROCESS FOR PRODUCING BENZO-PHENONE FROM 1,1-DIPHENYLETHANE (OR 1,1-DIPHENYLETHYLENE) USING ANTIMONATE CATALYSTS

BACKGROUND OF THE INVENTION

The present invention relates to a novel process for making benzophenone.

There are many known methods of manufacturing benzophenone. The best known method is the Fiedel-Crafts reaction. In this method aluminum chloride, benzene and carbon tetrachloride are reacted to form the intermediate dichlorophenylmethane which, upon hydrolysis, gives benzophenone. Benzophenone has also been made by a Friedel-Crafts reaction which involves condensation of benzene and phosgene in the presence of aluminum chloride. (German Pat. No. 403,507). The manufacture of benzophenone by condensation of benzene with benzoyl chloride by a non-catalytic or thermal process has been disclosed in U.S. Pat. No. 2,528,789. Benzophenone is also obtained from o-benzoylbenzoic acid by decarboxylation using a fluid-bed catalyst (Italian Pat. No. 542,862), and by decarboxylation in an inert heat-stable medium using a catalyst (French Pat. No. 994,850). A number of other methods are disclosed by patents. These patents disclose the oxidation of diphenylmethane with nitric acid (Swedish Pat. No. 137,686), oxidation of benzhydrol or diphenylmethane with chromic acid (U.S. Pat. No. 2,794,813) and oxidation of diphenylmethane with oxygen or air in the presence of a metal salt catalyst (U.S. Pat. No. 2,859,247).

Although the various techniques described in these patents are capable of producing benzophenone, they are each disadvantageous for various different reasons.

Accordingly, it is an object of the present invention to provide a new process for producing benzophenone which can be carried out in a simple and straight-forward manner to yield benzophenone in significant yields.

SUMMARY OF THE INVENTION

It has now been discovered that benzophenone can be produced by contacting 1,1-diphenylethane or 1,1-diphenylethylene with an antimonate catalyst in the presence of molecular oxygen. It has also been found that other 1,1-diaromatic alkanes or alkenes can be converted to corresponding diaromatic ketones by this process.

Therefore, the present invention provides a process for the catalytic oxidation of 1,1-diaromatic alkanes or alkenes to diaromatic ketones by contacting the diaromatic alkane or alkene reactant and an oxygen-containing gas with a catalyst comprising an antimonate. More specifically, the present invention provides a process for the catalytic oxidation of 1,1-diaromatic alkanes or alkenes to diaromatic ketones in which the 1,1-diaromatic alkanes or alkenes and oxygen are contacted with an antimonate catalyst comprising an oxide complex of antimony and at least one of the following: La, Th, U, rare earth, V, Ce, Cr and a metal or metalloid selected from Groups VA, VIA and VIII of the Periodic Table. In a specific embodiment, the present invention also provides a process for the vapor phase catalytic oxidation of 1,1-diphenylethane or 1,1-diphenylethylene to benzophenone in which the 1,1-diphenylethane or 1,1-diphenylethylene and oxygen are contacted with a catalyst comprising an oxide complex of antimony and uranium or an oxide complex of antimony and iron.

DETAILED DESCRIPTION

Reactants

The preferred reactants in this invention are 1,1-diaromatic alkanes or alkenes having the structure:

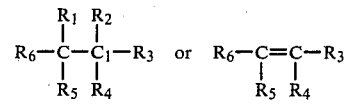

wherein
$R_1$, $R_2$, $R_3$ and $R_4$ are each independently selected from hydrogen and methyl; and
wherein
$R_5$ and $R_6$ are each independently selected from:
(1) unsubstituted phenyl;
(2) substituted phenyl substituted with 1 to 5 substituents selected from the group consisting of:

(a) $C_{1-8}$ alkyl;
(b) 

wherein R is $C_{0-6}$ alkyl and $R^1$ is $C_{1-6}$ alkyl;
(c) cyano; and
(d) $-R^2-C-OH$ wherein $R^2$ is $C_{0-6}$ alkyl;
(3) substituted phenyl substituted with one or two hydroxy groups; and
(4) substituted phenyl substituted with one or two acid anhydride groups of the formula:

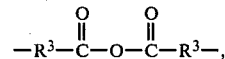

wherein $R^3$ is $C_{0-6}$ alkyl, with the proviso that two acid anhydride groups on a phenyl group are arranged para with respect to one another.

Preferred is the unsubstituted phenyl (1,1-diphenylethane or 1,1-diphenylethylene) or the substituted phenyl substituted with 1 to 4 substitutes selected from the group consisting of $C_{1-2}$ alkyl, cyano, and methyl carboxylic ester or substituted with 1 to 2 acid anhydride groups. Most preferred is 1,1-diphenylethane or 1,1-diphenylethylene.

Any source of molecular oxygen may be employed in the instant process. Air is the preferred source. The molar ratio of oxygen to the 1,1-diaromatic alkanes or alkenes in the reaction mixture should be in the range of 2.5:1 to 70:1 with a range of 10:1 to 50:1 being preferred.

Any material which is inert to the reactants, catalysts and products of the inventive reaction may be included in the reaction system as a diluent. For example, nitrogen gas could be added to the oxygen or benzene could be added to the 1,1-diaromatic alkanes or alkenes, if desired.

Process Conditions

In carrying out the inventive process, the 1,1-diaromatic alkanes and oxygen are contacted with a catalyst as described below for effecting the oxidation reaction. The inventive reaction can be accomplished both in the batch mode and continuously with both fixed- and fluid-catalyst beds. The instant reaction can also take place in either the gas phase or the liquid phase.

The reaction temperature is normally maintained between 200° and 600° C., preferably 300° to 500° C., and more preferably 375° to 475° C. The reaction pressure is normally maintained at atmospheric pressure but it may also be conducted at subatmospheric or superatmospheric pressure. The apparent contact time between the catalyst and the reactants may vary from about 0.1 to about 20 seconds for the fixed-bed process, preferably 1 to 10 seconds and more preferably about 3 seconds. The fluid-bed process has a corresponding range. In general, lower reaction temperatures require longer contact times and higher reaction temperatures require shorter contact times.

Catalyst

The catalysts employed in the inventive process comprise promoted antimonates. They can be described by the formula:

$$A_aSbO_x$$

wherein

A is V, Cr, La, Ce, rare earth elements, Th, U, Group VIII elements, Group VA elements, Group VIA elements or mixture thereof;
and wherein a is about 0.02 to 10; and
x is the number of oxygens sufficient to satisfy the valence requirements of the other elements present.

The catalysts may be any catalysts delineated by the general formula above with respect to the components of the catalysts. Preferred catalysts contain La, Ce, rare earth elements, Th, U, Group VIII elements, or mixture thereof; and more preferred catalysts contain Fe, Co, Ni and U. Even more preferred catalysts are those that contain Fe and U for these catalysts have been found to demonstrate superior activity. The proportion of the antimony and the promoter may vary widely. The Sb:A atomic ratio can range from 0.02:1 to 10:1. However, optimum activity appears to be obtained at ratios of about 0.1:1 to 0.5:1.

The catalysts can be employed in a supported or unsupported form. Preferred supports are the hydrous oxide gels, preferably silica and alumina. Any other known support material can be used which is stable under the reaction conditions to be encountered in the use of the catalyst and inert to the reaction system.

The exact chemical nature of the catalysts of the invention is not known. The catalyst may be a mixture of antimony oxide and iron oxide, for example, or an oxide complex of all the contained elements or a mixture thereof. In any event, these catalyst are generally known in the art and described inter alia in U.S. Pat. Nos. 3,308,151, U.S. 3,461,150, U.S. 3,431,292 and U.S. 3,435,061, the disclosures of which are incorporated herein by reference.

The catalysts of the present invention can be prepared from any mixture of compounds that can be calcined to give the desired oxide component. Preferably, the catalysts are prepared by coprecipitating decomposable salts such as nitrates, acetates, halides and/or oxides to form a catalyst precursor and then calcining the precursor in the presence of oxygen to form the catalyst. Other known catalyst preparation techniques, however, can be employed. Technique for preparing antimonate catalysts of the type used in the present invention are well known and shown, for example, in the various patents listed above.

Recovery

The reaction product obtained on completion of the reaction is normally in the form of a gas and composed primarily of 1,1-diaromatic alkenes, diaromatic ketones, carbon monoxide, carbon dioxide and unreacted 1,1-diaromatic alkanes or alkenes. This reaction product can be subjected to suitable known separation techniques to yield the desired end product, namely the diaromatic ketones.

For example, the product gas can be condensed and the reaction product separated from any carrier gas that may be in the system. The liquid reaction product can then be filtered to remove catalyst therefrom and then separated into component parts by the use of an acetone trap and distillation or by any other suitable separation technique.

As is well known, benzophenone and analogs thereof are used in perfumery for their odor and fixative properties. They also show bacteriostatic, fungicidal and insecticidal properties. Benzophenone can be used to accelerate the oxidation of linseed oil or to promote the copolymerization of drying oils and styrene monomer. They are also used in the flavoring and food industry as intermediates.

SPECIFIC EMBODIMENTS

In order to more thoroughly describe the present invention, the following working examples are presented. In each of these examples, 1,1-diphenylethane was oxidized in a 40 cc fixed-bed reactor equipped with stainless steel evaporation blocks. The top of the downflow reactor was packed with inert Alundum particles, which served as an evaporation zone. The reactor contained 10 cc Alundum and 30 cc catalyst. The gaseous feed (air) was introduced via a calibrated rotameter and the liquid feed was supplied directly into the reactor using a Sage syringe pump. The reactor was heated in a stainless steel block to give the desired reaction temperature.

In general, the experimental method consisted of supplying the liquid reactant, 1,1-diphenylethane, as a solution in an inert solvent (benzene), at concentration ranges of about 5 to 11 weight %. The 1,1-diphenylethane was oxidized in the presence of air by contact with an antimonate catalyst to produce benzophenone. The reactions were run at 375° C. to 475° C. at one atmosphere total pressure. Standard run conditions in all the examples, unless otherwise indicated, comprised an air/hydrocarbon ratio of 220/1 and a contact time of three seconds.

In all runs, the off gas was collected at the reactor exit and condensed to a liquid. The benzophenone was scrubbed from this liquid material in two acetone traps (second trap kept 0° C.). The liquid products were quantitatively analyzed using an H-P gas chromatograph. The tailgas was analyzed for $O_2$, $N_2$, CO and $CO_2$ using a Carle gas chromatograph.

For the purposes of this application, the following definitions are used:

$$\% \text{ conversion} = \frac{\text{g. carbon of 1,1-diphenylethane reacted}}{\text{g. carbon of 1,1-diphenylethane fed}} \times 100$$

% yield =

$$\frac{\text{g. carbon of 1,1-diphenylethane converted to product}}{\text{g. carbon of 1,1-diphenylethane fed}} \times 100$$

The results have all been adjusted to a 100% carbon balance.

The following experiments were conducted:

EXAMPLE 1

A catalyst system composed of an oxide complex of antimony and uranium, having a Sb:U atomic ratio of 4.6:1 was prepared as follows: 45.88 grams of uranyl acetate, $UO_2(C_2H_3O_2)_2 \cdot 2H_2O$, was dissolved in 1500 cc of distilled water. To this solution was then added 72.8 grams of antimony oxide, $Sb_2O_3$. The resultant slurry was heated to its boiling point and then refluxed for 18 hours. The paste was dried at 110° C. overnight and calcined at 940° C. for two hours. The reactor was charged with 30 cc of this catalyst. The reactor and catalyst were brought to a temperature of 475° C. A solution containing 5.54 g. 1,1-diphenylethane in 100 grams of benzene was then fed through the reactor. Along with the 1,1-diphenylethane, air was fed through the reactor at a rate of 192.18 cc/min. The reaction product was recovered over a period of 15 minutes and analyzed with the following results:
1,1-diphenylethane conversion=93%
benzophenone yield=46.2%
1,1-diphenylethylene yield=trace
carbon monoxide yield=12.9%
carbon dioxide yield=33.8%

EXAMPLE 2

Example 1 was repeated except that the reactor and catalyst were only brought to a temperature of 450° C. The following results were obtained:
1,1-diphenylethane conversion=78.6%
benzophenone yield=37.5%
1,1-diphenylethylene yield=0%
carbon monoxide yield=10.9%
carbon dioxide yield=30.2%

EXAMPLE 3

Example 1 was repeated except that the reactor and catalyst were only brought to a temperature of 425° C. The following results were obtained:
1,1-diphenylethane conversion=45.2%
benzophenone yield=18.7%
1,1-diphenylethylene yield=5.2%
carbon monoxide yield=5.4%
carbon dioxide yield=16.0%

EXAMPLE 4

A catalyst system composed of an oxide complex of antimony and iron, having an Sb:Fe atomic ratio of 2.5:1 was prepared as follows: 80.8 grams of ferric nitrate anhydride, $Fe(NO_3)_3 \cdot 9H_2O$, was dissolved in 1500 cc of distilled water. To this was added 72.8 grams of antimony oxide, $Sb_2O_3$. The resultant slurry was heated to boiling and then refluxed for 18 hours. This slurry was then evaporated to a thick brown paste. This paste was dried at 100° C. overnight and calcined at 274° C. for three hours. This material was then further calcined at 760° C. for two hours. The reactor was charged with 30 cc of this catalyst, the reactor and catalyst were then brought to a temperature of 375° C. A solution containing 5.54 grams of 1,1-diphenylethane in 100 grams of benzene was then fed through the reactor. Along with this 1,1-diphenylethane, air was fed through the reactor at a rate of 192.18 cc/min. The reaction product was recovered over a period of 15 minutes and analyzed with the following results:
1,1-diphenylethane conversion=92.0%
benzophenone yield=8.3%
1,1-diphenylethylene yield=10.6%
carbon monoxide=9.2%
carbon dioxide yield=63.9%

Although only a few embodiments of the present invention have been specifically described above, it should be appreciated that many additions and modifications can be made without departing from the spirit and scope of the invention. These and all other modifications are intended to be included within the scope of the present invention, which is to be limited only by the following claims

We claim:

1. A process for forming diaromatic ketones comprising oxidizing at a temperature of about 200° C.–600° C. a compound of the formula:

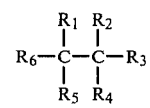

wherein
$R_1$, $R_2$, $R_3$ and $R_4$ are each independently selected from hydrogen and methyl; and
wherein $R_5$ and $R_6$ are each independently selected from;
(1) unsubstituted phenyl;
(2) substituted phenyl substituted with 1 to 5 substituents selected from the group consisting of:
(a) $C_{1-8}$ alkyl;
(b)

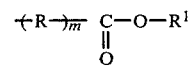

wherein R is $C_{1-6}$ alkyl, $R^1$ is $C_{1-6}$ alkyl and m is 0 or 1; and
(c) cyano;
(3) substituted phenyl substituted with one or two hydroxy groups; and
(4) substituted phenyl substituted with one or two acid anhydride groups of the formula

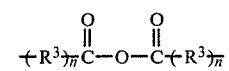

wherein $R^3$ is $C_{1-6}$ alkyl and n is 0 or 1, with the proviso that two acid anhydride groups on a phenyl group are arranged para with respect to one another;
over an oxide catalyst of the formula:

wherein A is V, Cr, La, Ce, a rare earth element, Th, U, a Group VIII element, a Group VA element, a Group VIA element or mixture thereof;
and wherein a is about 0.02 to 10; and
x is the number of oxygens sufficient to satisfy the valence requirements of the other elements present.

* * * * *